United States Patent [19]

Immel et al.

[11] Patent Number: 4,902,661
[45] Date of Patent: Feb. 20, 1990

[54] RHODIUM CATALYSTS, PROCESS FOR THEIR PREPARATION AND PROCESS FOR THE PREPARATION OF SUBSTITUTED OR UNSUBSTITUTED DIPHENYLAMINE BY USING THE RHODIUM CATALYSTS

[75] Inventors: Otto Immel; Hans-Helmut Schwarz, both of Krefeld, Fed. Rep. of Germany

[73] Assignee: Bayer Aktiengesellschaft, Leverkusen, Fed. Rep. of Germany

[21] Appl. No.: 294,833

[22] Filed: Jan. 9, 1989

[30] Foreign Application Priority Data

Jan. 22, 1988 [DE] Fed. Rep. of Germany ....... 3801754

[51] Int. Cl.<sup>4</sup> ................. B01J 21/18; B01J 27/053; B01J 20/00
[52] U.S. Cl. ............................. 502/184; 502/218; 502/243; 502/313; 502/330; 564/45; 564/462
[58] Field of Search ............... 502/184, 243, 313, 330, 502/322, 333, 334, 218, 184; 564/450, 462

[56] References Cited

U.S. PATENT DOCUMENTS

4,057,581 11/1977 Krall et al. ........................ 502/313

FOREIGN PATENT DOCUMENTS

0053817 6/1982 European Pat. Off. .
0123233 10/1984 European Pat. Off. .
0208933 1/1987 European Pat. Off. .
2367035 5/1978 France .

*Primary Examiner*—H. M. S. Sneed
*Assistant Examiner*—J. Saba
*Attorney, Agent, or Firm*—Sprung, Horn, Kramer & Woods

[57] ABSTRACT

Diphenylamine which is unsubstituted or substituted by alkyl or alkoxy groups can be prepared by treating appropriately substituted dicyclohexylamine with 1–10 bar of $H_2$ over catalysts containing 0.05–5% by weight of rhodium at 250°–450° C. In addition to rhodium, the catalysts contain at least one other platinum metal from the group consisting of palladium, platinum and iridium on a support containing the noble metals in a total amount of 0.05–5% by weight, the percentage by weight of rodium with respect to all noble metals being 10–90%, and furthermore containing additives of 1–6% by weight of an alkali metal hydroxide and 1–6% by weight of an alkali metal sulphate. All percentages are based on the total weight of the catalyst.

14 Claims, No Drawings

RHODIUM CATALYSTS, PROCESS FOR THEIR PREPARATION AND PROCESS FOR THE PREPARATION OF SUBSTITUTED OR UNSUBSTITUTED DIPHENYLAMINE BY USING THE RHODIUM CATALYSTS

BACKGROUND OF THE INVENTION

The invention relates to novel rhodium catalysts and also to a process for their preparation. These novel rhodium catalysts are suitable in particular for the preparation of substituted or unsubstituted diphenylamine from appropriately substituted dicyclohexylamine, as a result of which the invention furthermore relates to their use in a process for the preparation of this substituted or unsubstituted diphenylamine by using rhodium catalysts.

DE-OS (German Published Specification) 2,331,878 discloses a process for the preparation of diphenylamine and derivatives thereof, in which the starting materials are imines such as N-cyclohexylidene-aniline and derivatives thereof which are dehydrogenated in the gas phase in the presence of supported catalysts based on nickel, platinum, palladium or copper/chromium. N-cyclohexylidene-aniline, for example, is prepared from cyclohexanone and aniline by condensation.

Furthermore, DE-OS (German Published Specification) 2,520,893 discloses to prepare diphenylamine by catalytic dehydrogenation of compounds and/or compound mixtures consisting entirely or partly of hydrogenated diphenylamine in the presence of a dehydrogenation catalyst containing nickel/chromium, aluminium, copper, manganese and alkali. Compounds of this type shown in the working examples are binuclear aromatic imines.

A further process known from Kinet, Katal. 28 (1), 250-254 (quoted in C.A. 107 (23), 217420 z) finally shows that in addition to the dehydrogenating aromatization a cyclization to the carbazole also has to be taken into account when using hydrogenation/dehydrogenation catalysts. For example, using Pt (1%)/$Al_2O_3$ at 380° C., N-cyclohexylaniline yields 41% of carbazole and only 18% of diphenylamine; under similar conditions, dicyclohexylamine yields 41% of carbazole and onlt 17% diphenylamine, and N-cyclohexylidene-aniline yields 40% of carbazole and 20% of diphenylamine. In addition, deamination and rearrangement products such as aniline, benzene, diphenyl and 4-amino-diphenyl are observed.

The processes mentioned yield insufficient conversions and yields and as a process to be carried out industrially they are in need of improvement in every respect. The desire to provide a process to be carried out industrially in a simple manner and ensuring high yields and allowing easy work-up of the reaction products is satisfied by the invention.

SUMMARY OF THE INVENTION

The invention relates to catalysts containing rhodium and at least one other platinum metal from the group consisting of palladium, platinum and iridium on supports containing the noble metals in a total amount of 0.05-5% by weight, preferably 0.05-4% by weight, particularly preferably 0.1-3% by weight, the percentage by weight of rhodium with respect to all noble metals being 10-90%, preferably 15-80%, particularly preferably 20-70%, and furthermore containing additives of 1-6% by weight of an alkali metal hydroxide and 1-6% by weight of an alkali metal sulphate, all percentages being based on the total weight of the catalyst.

DETAILED DESCRIPTION OF THE INVENTION

An important feature of the catalyst according to the invention is the combination of rhodium with at least one of the other platinum metals mentioned. Preferably, rhodium is combined with palladium or platinum or a mixture of palladium and platinum. Partcularly preferably, palladium or platinum by itself is used for the combination with rhodium.

Furthermore, the catalyst according to the invention contains 1-6% by weight, preferably 2-5% by weight, relative to the total weight of the catalyst, of an alkali metal hydroxide such as lithium hydroxide, sodium hydroxide, potassium hydroxide, rubidium hydroxide, caesium hydroxide, preferably lithium hydroxide, sodium hydroxide, potassium hydroxide, particularly preferably sodium hydroxide or potassium hydroxide. Furthermore, the catalyst according to the invention additionally contains in the combination with one or more of the alkali metal hydroxides mentioned 1-6% by weight, preferably 2-5% by weight, relative to the total amount of the catalyst, of an alkali metal sulphate such as lithium sulphate, sodium sulphate, potassium sulphate, rubidium sulphate, caesium sulphate, preferably lithium sulphate, sodium sulphate, potassium sulphate, particularly preferably sodium sulphate or potassium sulphate.

The constituents mentioned of the catalysts according to the invention are disposed on a support. Examples of such supports are aluminum oxide, aluminum spinel, activated carbon, kieselguhr, bentonite, pumice, silica gel, $ZrO_2$, $TiO_2$, ZnO, MgO and also oxides of the rare earths.

The constituents mentioned of the catalysts according to the invention are preferably applied to a support of aluminum oxide or an aluminum spinel, particularly preferably to an $Al_2O_3$ or Al spinel which has been treated with chromium and manganese. Examples of aluminum oxide are particularly α- and γ-modification. Aluminum spinels are compounds of the formula Me(II)$Al_2O_4$ or Me(I)$AlO_2$ in which Me(II) is a divalent metal cation of iron, zinc, nickel, copper, cobalt, cadmium, magnesium or others, preferably of magnesium, and Me(I) is a monovalent cation, for example lithium (lithium/aluminum spinel). In the spinels, aluminum can be replaced in part by trivalent iron, chromium or manganese. Preferably, $Al_2O_3$, particularly preferably γ-$Al_2O_3$, is used. Such a support usually has particularly preferably a combined chromium and manganese content of about 0.05-8% by weight, preferably 0.2-5% by weight, relative to the total weight of the catalyst. The ratio by weight of chromium and manganese is about 5:1-1:5, preferably 10:9-1:2. Such supports treated with chromium and manganese are known from EP 208,933.

The catalysts according to the invention described can be prepared in the particularly preferred manner by applying compounds of chromium and manganese to an $Al_2O_3$ or an aluminum spinel in the form of extrudates, pills or balls having dimensions of about 2-10 mm, heating the support thus treated to an elevated temperature, subsequently applying separately the noble metals and one or more alkali metal hydroxides and one or more alkali metal sulphates; after each application, the support is dried, in general at 100°-140° C. at reduced to atmospheric pressure, such as 1-1000 mbar, preferably 10-500 mbar, for example at an aspirator vacuum.

The application of chromium and manganese to the catalyst support in the particularly preferred manner can, for example, be carried out by coprecipitation of a manganese/chromium hydroxide mixture from a chromium salt and manganese salt solution using alkali metal hydroxide solution or ammonia, followed by removal of the soluble components by washing with water. Suitable chromium salts and manganese salts are in particular the sulphates, chlorides, acetates and/or nitrates of the elements mentioned. The precipitation of the chromium and manganese on the catalyst support can also be carried out in the form of ammonium/manganese chromate or ammonium/alkali metal/manganese chromate from a solution of manganese(II) salts and ammonium dichromate by means of ammonia and/or basic alkali compounds. Particularly uniform and adhesive precipitations are obtained by adding the base slowly and evenly and avoiding large differences in concentration. To this end, the precipitation can be carried out, for example, by means of urea under hydrolytic conditions, which ensures the conditions of slow addition of base in a particularly efficient manner.

After the application of the chromium and manganese compounds and their precipitation described, the catalyst support thus treated is washed until free of soluble compounds, before it is heated to elevated temperatures (about 200°-450° C., preferably 250°-350° C.). After this heat treatment, the support treated with chromium and manganese is ready to be impregnated with the remaining catalyst constituents mentioned.

The impregnation of the support with the noble metals or with alkali metal hydroxide and alkali metal sulphate (one or more of each of these) is carried out separately. This can be done by first impregnating the support with the noble metals, for example in the form of aqueous solutions of their chlorides, nitrates, acetates or other suitable salts, after drying a further impregnation being carried out using an alkali metal hydroxide solution and an alkali metal sulphate solution. In this treatment, the noble metals are precipitated in the form of their oxides or hydroxides. The impregnation of the alkali metal hydroxide or hydroxides and the alkali metal sulphate or sulphates can be carried out separately or at the same time. After a final drying operation, the catalyst according to the invention is ready for use. Before being used, it is preferably activated in a reactor by treating it with hydrogen at an elevated temperature, such as at 120°-400° C., preferably at 150°-380° C.

It is also possible initially to impregnate the support with an alkali metal hydroxide solution, then to dry it and apply the noble metal salts mentioned to the catalyst support thus pretreated and made alkaline, the precipitation of the noble metals in the form of their oxides or hydroxides taking place at the same time as the impregnation. In this variation, the additional impregnation with one or more alkali metal sulphates together with the alkali metal hydroxide can be carried out before or after the application of the alkali metal hydroxide or as a final drying operation after the application of the noble metals. In this case, too, a separate drying operation is carried out after each impregnation. In this variation, too, the catalyst is ready for use after the final drying operation and can be first activated in the manner described using hydrogen at an elevated temperature.

Instead of applying the substances mentioned to the support mentioned by impregnation, it is also possible to spray it with a suitable solution. The required apparatuses and the adjustment of the level of substances used by choosing the amount and concentration of the solutions of the elements mentioned is known in principle to one skilled in the art.

In addition to aqueous solutions, alcoholic solutions or solutions in lower carboxylic acids or lower amines are in principle also suitable, provided the intended salts of the noble metals or the basic alkali metal compounds are soluble therein.

The catalysts according to the invention are highly suitable for the dehydrogenation of substituted or unsubstituted dicyclohexylamine to substituted or unsubstituted diphenylamine, in which outstandingly high activities and selectivities are observed.

Accordingly, the invention furthermore relates to a process for the preparation of diphenylamine of the formula

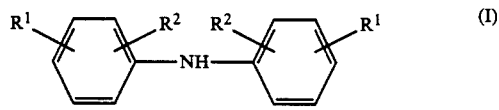

in which
R$^1$ and R$^2$ independently of one another denote hydrogen, C$_1$-C$_4$-alkyl or C$_1$-C$_4$-alkoxy,
which is characterized in that dicyclohexylamines of the formula

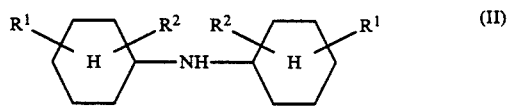

in which
R$^1$ and R$^2$ have the above meaning,
are treated over a catalyst containing 0.05-5% by weight of rhodium on a support at 250°-450° C. and 1-20 bar.

The process according to the invention is preferably carried out in such a manner that the rhodium catalyst used is the catalyst according to the invention described.

The radicals R$^1$ and R$^2$ independently of one another denote hydrogen, C$_1$-C$_4$-alkyl or C$_1$-C$_4$-alkoxy. Examples of the alkyl or alkoxy substituents mentioned are: methyl, ethyl, propyl, isopropyl, butyl, isobutyl, methoxy, ethoxy, propoxy, isopropoxy, butoxy or isobutoxy. Preferably, the substituents mentioned have 1-2 C atoms, particularly preferably they are methyl or methoxy. Furthermore, preferably one of the substituents R$^1$ and R$^2$ denotes hydrogen, while the other substituent denotes alkyl or alkoxy to the extent mentioned. Particularly preferably, the process is aimed at preparing unsubstituted diphenylamine.

The process according to the invention is carried out at a temperature of 250°-450° C., preferably 300°-400° C., and a pressure of 1-10 bar, preferably 1-6 bar, in the gas phase. In a manner known to one skilled in the art, in general lower temperatures within the range mentioned are correlated to lower pressures of the range also disclosed and vice versa, with the result that the reaction mixture remains in the gas phase.

The substituted or unsubstituted dicyclohexylamine to be reacted can of course be used as such according to the invention. However, it is a particular advantage that dicyclohexylamine can also by used as a mixture with other substances. These other substances are, for example, substituted or unsubstituted cyclohexylamine, which may be additionally present, or a mixture of substituted or unsubstituted cyclohexylamine and accordingly substituted N-cyclohexylaniline, which may be additionally present. Furthermore, substituted or unsubstituted aniline can be present, which, for example, had not been completely converted during the preparation of the dicyclohexylamine.

Dicyclohexylamine or its mixture with one or more of the substances mentioned is passed over the rhodium catalyst advantageously by means of an inert carrier gas stream. Examples of suitable inert carrier gases are nitrogen, hydrogen, argon, lower hydrocarbons such as methane or ethane and others or mixtures consisting of these carrier gases. Preferably, nitrogen or hydrogen or a mixture thereof is used as the inert carrier gas. A residual amount of ammonia, for example from the step of the dicyclohexylamine preparation, is not detrimental either to the process according to the invention. The amount of carrier gas used is 1–100 l/g of starting material, preferably 1–50 l/g of starting material. The space velocity through the catalyst is set at 0.01–1 kg of starting material per liter of catalyst and hour.

The absence of any adverse effects of components in the mixture of dicyclohexylamine of the type described above makes it possible to use, in an advantageous variation, a mixture resulting from the reductive alkylation of aniline with hydrogen. In particular, this reductive alkylation of aniline with hydrogen is carried out at 150°–220° C. over a ruthenium catalyst. Particularly preferably, this reductive alkylation of aniline is carried out over a catalyst containing ruthenium and palladium on a support, preferably a support from the group consisting of $Al_2O_3$ and aluminum spinel containing the noble metals in a total amount of 0.05–5% by weight, preferably 0.1–4% by weight, particularly preferably 0.1–3% by weight, and a weight ratio of ruthenium to palladium such as 1:9–9:1, preferably 2:8–8:2, particularly preferably 3:7–7:3, and furthermore 0.1–10% by weight, preferably 0.2–5% by weight, of an alkaline alkali metal compound, all percentages being based on the total weight of the ruthenium-containing catalyst.

These catalysts are mainly distinguished by the combination of ruthenium with palladium and, compared to the catalyst containing only ruthenium, have a significantly higher service life, which is indispensable for their use in an industrial process.

Alkaline alkali metal compounds for these catalysts containing ruthenium and other platinum metals are: the oxides, hydroxides, alcoholates or salts of weak acids of lithium, sodium, potassium, rubidium or caesium, preferably the hydroxides, alcoholates and salts of weak acids of lithium, sodium or potassium, particularly preferably of sodium or potassium. Examples of weak acids are carbonic acid, acetic acid, formic acid and other carboxylic acids whose alkali metal salts have an alkaline reaction and are in any case those which are free of nitrogen, halogen, sulphur and other elements known as hydrogenation catalyst poisons. Alcoholates are for example those of methanol, ethanol, propanol, butanol and other alcohols.

$Al_2O_3$ or aluminum spinels, which are preferred as supports for these ruthenium catalysts, are the same as the ones disclosed above. These ruthenium catalysts can be prepared by separate application of the noble metals and the alkaline alkali metal compounds in a manner quite similar to that described above for the rhodium catalysts.

Such a reductive alkylation of aniline with hydrogen at 150°–220° C. over ruthenium catalysts is carried out at a pressure of 0.5–10 bar, preferably 0.5–4 bar, particularly preferably 0.7–2 bar. The space velocity through the catalyst is 0.05–2 kg, preferably 0.1–0.5 kg, of aniline per liter of catalyst and hour. The amount of dicyclohexylamine is increased if a lower temperature within the range mentioned is established; this finding is important for the case where such an alkylation mixture having a high dicyclohexylamine content is used directly for the preparation of diphenylamine according to the invention.

The pressure range for the reductive alkylation of aniline with hydrogen over a ruthenium catalyst overlaps largely with the pressure range of the preparation of diphenylamine according to the invention. This makes it possible, in a further advantageous variation, to carry out the steps of reductive alkylation of aniline and dehydrogenation of the dicyclohexylamine present in such an alkylation mixture to give, according to the invention, diphenylamine in a reactor (or two reactors connected in direct series) in such a manner that substituted or unsubstituted aniline, hydrogen and the recycling substances mentioned below are passed through two consecutive catalyst beds, the first of which contains a ruthenium catalyst and is maintained at a temperature of 150°–220° C. and the second of which contains a rhodium catalyst and is maintained at 250°–450° C.

In this advantageous variation, dicyclohexylamine cyclohexylamine and N-cyclohexyl-aniline are formed from aniline and hydrogen in the first stage, unconverted aniline and hydrogen and ammonia which is also formed being additionally present. This mixture without isolation of the intermediates is passed through the second catalyst bed, hydrogen and ammonia functioning as carrier gas (possibly as a mixture with nitrogen which had been used in the first stage as the carrier gas). In the second stage, dicyclohexylamine and N-cyclohexyl-aniline are converted according to the invention to diphenylamine (or substituted diphenylamines disclosed above). All components of the resulting reaction mixture which have not been converted to diphenylamine can be passed to the stage of the reductive alkylation of aniline. This recycling represents a significant improvement of the economy of the entire process. It may be useful to wash out or condense by compression some of the ammonia present in the recycling mixture. It is of course also possible to separate the recycling mixture by another method, which is in principle known to one skilled in the art, and to remove selectively components from the recycling mixture.

The advantageous combination of reductive alkylation of aniline and the subsequent preparation of diphenylamine according to the invention makes it furthermore possible to utilize the heat of the reaction of the reductive alkylation stage in the second stage of the preparation of diphenylamine according to the invention.

In terms of the combination mentioned of the two reaction stages, it is furthermore a particular advantage if in the first stage the specifically mentioned ruthenium catalyst containing palladium and containing the alkaline alkali metal compound is used since this catalyst produces a very large amount of dicyclohexylamine, a large amount of N-cyclohexyl-aniline but a very small amount of undesired by-products such as cyclohexane and benzene.

EXAMPLE 1

50 g of a $\gamma$-$Al_2O_3$ in the form of pellets to which chromium and manganese had been applied according to European Patent Application 0,208,933, Example 1, were evenly impregnated in a round-bottomed flask with a solution of 0.66 g of $RhCl_3$ and 0.83 g of $H_2PtCl_6$ in 15 ml of water. The moist catalyst pellets were dried at 120° C. at an aspirator vacuum and then impregnated again with a solution of 1.46 g of NaOH in 15 ml of water and dried again. The pellets were then impregnated again with a solution of 1.5 g of $K_2SO_4$ in 15 ml of water and dried again.

A reaction tube having a diameter of 17 mm and a length of about 600 mm and whose upper part served as evaporation zone and which was packed in the lower part with 30 ml of the catalyst produced was maintained at 380° C. by electric heating. At this temperature, the catalyst was first activated for 16 hours in an $H_2$ stream. Using a calibrated metering device, 29.7 g of dicyclohexylamine and 10 l of $H_2$/h were passed through the reaction tube over a period of 3 hours. The reaction product was condensed and analyzed by gas chromatography.

It had the following composition:
Diphenylamine: 92.4%
N-cyclohexyl-aniline: 3.1%
Aniline: 3.4%
Benzene: 0.4%
By-products: balance

EXAMPLE 2

100 g of a $\gamma$-$Al_2O_3$ in spherical form (2 to 6 mm) to which manganese and chromium had been applied according to European Patent Application 0,208,933, Example 1, were impregnated with a solution which had been prepared from 0.79 g of $RhCl_3$, 2.50 g of $PdCl_2$, 0.8 g of concentrated hydrochloric acid and 34 ml of water. The moist catalyst pellets were dried at 120° C. at an aspirator vacuum.

50.5 g of the catalyst pellets were first impregnated with a solution of 2.75 g of KOH in 15 ml of water and, after drying of the intermediate product, they were impregnated repeatedly with a solution of 1.5 g of $K_2SO_4$ in 15 ml of water and dried again at 120° C.

30 ml (27.2 g) of the catalyst thus prepared were heated using the reaction tube described in Example 1 in a hydrogen stream (10 l/h) to 400° C. and maintained at this temperature for 20 hours. The temperature of the furnace was then reduced, and the dehydrogenation reaction carried out at 360° to 380° C. 5.1 g of dicyclohexylamine and 10 l of hydrogen or 10 l of nitrogen were both passed through the catalyst. Depending on the time on stream of the catalyst, the reaction product had the following composition:

| | Time on Stream of the catalyst: | | | | |
|---|---|---|---|---|---|
| | 220 | 316 | 388 | 681 | 1016 h |
| Diphenylamine | 94.3 | 96.8 | 94.6 | 95.7 | 94.0% |
| N—Cyclohexylaniline | 0.4 | 0.7 | 0.4 | 0.7 | 1.4% |
| Aniline | 4.6 | 2.0 | 4.0 | 2.9 | 3.1% |

-continued

| | Time on Stream of the catalyst: | | | | |
|---|---|---|---|---|---|
| | 220 | 316 | 388 | 681 | 1016 h |
| By-products | balance | balance | balance | balance | balance |
| Carrier gas | $H_2$ | $N_2$ | $H_2$ | $N_2$ | $N_2$ |

EXAMPLE 3

In this example, aniline served as the starting material for the preparation of diphenylamine. In this case, two reaction tubes (internal diameter=17 mm), on top of each other were used, each of which was filled with different catalysts and also maintained at different temperatures. In the first (upper) reaction tube, 30 ml of a catalyst containing Ru (0.5%) and Pd (0.5%) on $Al_2O_3$ which had been treated with 4% strength NaOH were present.

This catalyst bed was maintained at 180° C.

This catalyst had been prepared as follows: 500 g of a commercially available $\gamma$-$Al_2O_3$ (spherical diameter: 2–5 mm) having a specific surface area of 350 m²/g were impregnated with a solution of 20 g of NaOH in 170 ml of water and subsequently dried. 100 g of the $Al_2O_3$ thus treated were impregnated with a solution of 2.5 g of $RuCl_3$ and 0.83 g of $PdCl_2$ in 30 ml of water, subsequently dried at 120° C. and then activated at 250° C. in a hydrogen stream for 2 hours.

The reaction tube containing the catalyst prepared in this manner was connected to a second tube, in which 30 ml of a catalyst as in Example 1 were present and which was maintained at a temperature of 380° C. 90 g of aniline in combination with 10 l of $H_2$/h were passed into the reaction tubes thus connected in series over a period of 21.5 hours. The reaction product leaving the second reaction tube was condensed and analyzed. Analysis showed the following composition:

Diphenylamine: 60.4%
Cyclohexylamine: 0.4%
N-cyclohexyl-aniline: 6.3%
Aniline: 32.3%
By-products: balance The mixture remaining after diphenylamine had been separated off was recycled.

The uncondensed flue gas was also recycled after some of the $NH_3$ had been removed.

What is claimed is:

1. A catalyst containing rhodium and at least one other platinum metal from the group consisting of palladium, platinum and iridium on supports containing the noble metals in a total amount of 0.05–5% by weight, the percentage by weight of rhodium with respect to all noble metals being 10–90%, and furthermore containing additives of 1–6% by weight of an alkali metal hydroxide and 1–6% by weight of an alkali metal sulphate, all percentages being based on the total weight of the catalyst.

2. The catalyst of claim 1 containing the noble metals in a total amount of 0,05–4% by weight.

3. The catalyst of claim 2 containing the noble metals in a total amount of 0.1–3% by weight.

4. The catalyst of claim 1 wherein the percentage by weight of rhodium with respect to all noble metals is 15–80%.

5. The catalyst of claim 4 wherein the percentage by weight of rhodium with respect to all noble metals is 20–70%.

6. The catalyst of claim 1 wherein the other noble metal is palladium or platinum or a mixture of palladium and platinum.

7. The catalyst of claim 6 wherein the other noble metal is palladium or platinum by itself.

8. The catalyst of claim 1 containing 2–5% by weight of an alkali metal hydroxide such as LiOH, NaOH, KOH, RbOH or CsOH.

9. The catalyst of claim 1 containing 2–5% by weight of an alkali metal sulphate such as $Li_2SO_4$, $Na_2SO_4$, $K_2SO_4$, $Rb_2SO_4$ or $Cs_2SO_4$.

10. The catalyst of claim 1 wherein the catalyst support is one of the group of aluminum oxide, aluminum spinel, activated carbon, kieselgur, bentonite, pumice, silica gel, $ZrO_2$, $TiO_2$, ZnO, MgO or an oxide of the rare earths.

11. The catalyst of claim 1, wherein the support is $Al_2O_3$ or an aluminum spinel.

12. The catalyst of claim 11, wherein the support is $Al_2O_3$ treated with chromium and manganese or an aluminum spinel thus treated.

13. The catalyst of claim 12 wherein the support has a combined chromium and manganese content of 0.05–8% by weight, relative to the total weight of the catalyst and a ratio by weight of chromium and manganese of 5:1–1:5.

14. A process for the preparation of catalysts according to claim 1, characterized in that a support is impregnated in separate processes with an aqueous solution of the noble metals sufficient to apply the amount of noble metal mentioned to the support, and is impregnated with aqueous solutions of alkali metal hydroxide and alkali metal sulphate and the catalysts are dried after each impregnation process.

* * * * *